United States Patent
Chin et al.

(10) Patent No.: US 6,187,987 B1
(45) Date of Patent: Feb. 13, 2001

(54) RECOVERY OF AROMATIC HYDROCARBONS USING LUBRICATING OIL CONDITIONED MEMBRANES

(75) Inventors: Arthur A. Chin, Cherry Hill, NJ (US); Bryan M. Knickerbocker, Beaumont, TX (US); Jeffrey C. Trewella, Kennett Square, PA (US); Terry R. Waldron, PT Neches, TX (US); Lloyd S. White, Columbia, MD (US)

(73) Assignee: Exxon Mobil Corporation, Fairfax, VA (US)

( * ) Notice: Under 35 U.S.C. 154(b), the term of this patent shall be extended for 0 days.

(21) Appl. No.: 09/126,256

(22) Filed: Jul. 30, 1998

(51) Int. Cl.$^7$ .................................................. C07C 7/144
(52) U.S. Cl. ......................... 585/819; 585/818; 210/654; 260/674
(58) Field of Search ................................... 585/818, 819; 210/654; 260/674

(56) References Cited

U.S. PATENT DOCUMENTS

| | | | |
|---|---|---|---|
| 4,115,465 | 9/1978 | Elfert et al. | 260/674 R |
| 4,571,444 | * 2/1986 | Black et al. | 585/819 |
| 4,872,967 | 10/1989 | Clem et al. | 208/65 |
| 4,879,044 | 11/1989 | Feimer et al. | 210/654 |
| 4,946,594 | 8/1990 | Thaler et al. | 210/651 |
| 4,975,178 | 12/1990 | Clem et al. | 208/65 |
| 5,019,666 | 5/1991 | Satori et al. | 585/519 |
| 5,039,418 | 8/1991 | Schucker | 210/640 |
| 5,093,003 | 3/1992 | Ho et al. | 210/640 |
| 5,095,171 | 3/1992 | Feimer et al. | 585/819 |
| 5,159,130 | 10/1992 | Sartori et al. | 585/819 |
| 5,290,452 | 3/1994 | Schucker | 210/640 |
| 5,396,019 | 3/1995 | Sartori et al. | 585/819 |
| 5,416,259 | 5/1995 | Darnell et al. | 585/804 |
| 5,635,055 | 6/1997 | Sweet et al. | 208/99 |
| 5,643,442 | 7/1997 | Sweet et al. | 208/302 |

OTHER PUBLICATIONS

W.S. Winston Ho, Ph.D. and Kamalesh K. Sirkar, Ph.D., "Membrane Handbook", pp. 152–157—no date.
Robert C. Binning and Frank E. James, "Permeation: A new way to separate mixtures", The Oil and Gas Journal (1958), pp. 104–105—no month.
R. W. Baker et al., Membrane Separation Systems A Research & Development Needs Assessment, Final Report vol. II (1990), pp. (2) i–38—Mar.
S. Sourirajan, "Reverse Osmosis", Chapter 7 (1970), pp. 409–428—no month.
R. Rautenbach and R. Albrecht, "The Separation Potental of Pervaporation" Part 1, Journal of Membrane Science, vol. 25 (1985), pp. 1–23—no month.
R. Rautenbach and R. Albrecht, "The Separation Potential of Pervaporation" Part 2 , Journal of Membrane Science, vol. 25 (1985), pp. 25–54—no month.
Xianshe Feng and Robert Y.M. Huang, "Liquid Separation by Membrane Pervaporation: A Review", Ind. Eng. Res. 1997, vol. 36, pp. 1048–1066—no month.
Robert C. Schucker, "Hollow Fiber Permeators for the Separation of Aromatic from Aliphatic Molecules in Transporation Fuels", 1995, pp. 375–379—no month.
A. Iwama and Y. Kazuse, "New Polyimide Ultrafiltration membranes for organic use", Journal of Membrane Science, vol. 11 (1982), pp. 297–309—no month.

* cited by examiner

Primary Examiner—Walter D. Griffin
Assistant Examiner—Nadine Preisch
(74) Attorney, Agent, or Firm—Malcolm D. Keen (57) ABSTRACT

Permselective separation of aromatic hydrocarbons from non-aromatic hydrocarbons in a feed stream is accomplished using improved asymmetric membranes. The preferred membranes are fashioned from a polyimide and conditioned with a lubricating oil. Feed streams containing a mixture of aromatic and non-aromatic hydrocarbons are contacted with the dense active layer side of the polyimide membrane under a pressure and temperature sufficient to selectively permeate the desired aromatic hydrocarbon.

30 Claims, 4 Drawing Sheets

RECOVERY OF AROMATIC HYDROCARBONS USING LUBRICATING OIL CONDITIONED MEMBRANES

FIELD OF INVENTION

The present invention relates a method of using membranes for the separation of aromatic hydrocarbons from non-aromatic hydrocarbons.

Of particular interest, the membranes are useful for the recovery of aromatic hydrocarbons, e.g. toluene, having a high purity from process streams containing aromatic and non-aromatic hydrocarbons in a commercial process for the production of aromatic hydrocarbons.

BACKGROUND OF THE INVENTION

Aromatic hydrocarbons (benzene, toluene, xylenes, etc.) serve as important precursors in the production of petrochemicals such as nylon, polyurethanes, polyesters, resins, and plasticizers. These petrochemicals are for the most part commodities, where the product conforms to a common specification with limited opportunity for differentiation.

A key to profitability in the petrochemical industry is to create and maintain a sustainable cost advantage over competitors. The cash cost of production is a critical factor, of which a significant portion is related to raw materials cost and utilities. While there is in principle no shortage of aromatics feed for production of petrochemicals, the cost of feed can vary significantly depending on the source of the feed. For example, a traditional way to recover high-purity aromatics is distillation, followed by liquid/liquid extraction, followed by further distillation. The liquid/liquid extraction step is expensive, due in part to the costs involved in purchase and recovery of the extraction solvent. A lower-cost alternative is to avoid the extraction step, and recover aromatics via distillation alone. However, distilled feeds contain co-boiling non-aromatics and other impurities that may impact yields and operations of the subsequent conversion process.

The separation of aromatics from non-aromatics is useful in upgrading aromatics-containing streams in petroleum refineries, such streams including naphtha streams, heavy catalytic naphtha streams, intermediate catalytic naphtha streams, light aromatic streams and reformate streams, and in chemical operations for the recovery of aromatics such as benzene, toluene, xylenes, naphthalene, etc.

The use of membranes to separate aromatics from saturates has long been pursued by the scientific and industrial community. Methods of membrane separation include hyperfiltration, also known as reverse osmosis (RO) in aqueous separations, pervaporation and perstraction. Pervaporation relies on vacuum on the permeate side to evaporate the permeate from the surface of the membrane and maintain the concentration gradient driving force which drives the separation process. In perstraction, the permeate molecules in the feed diffuse into the membrane film, migrate through the film and reemerge on the permeate side under the influence of a concentration gradient. A sweep flow of liquid or gas is used on the permeate side of the membrane to maintain the concentration gradient driving force. In contrast, hyperfiltration does not require the use of external forces on the permeate side of the membrane, but drives the separation through application of a pressure gradient across the membrane.

Early work with hyperfiltration or reverse osmosis, using cellulose acetate and polyethylene films showed some aromatics enrichment but at low membrane fluxes (Sourirajan, S., *Reverse Osmosis*, Academic Press, 1970). Subsequent studies demonstrated that the separation potential of a pervaporation system is much higher than that of RO (Rautenbach, R. and Albrecht, R., Journal of Membrane Science, 25, 1–54, 1985).

Membrane separation of aromatics from saturates has been the subject of numerous patents.

U.S. Pat. No. 3,370,102 discloses a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 discloses the separation of hydrocarbons by type, i.e., aromatic, unsaturated, saturated, by permeating a portion of the mixture through a non-porous cellulose ether membrane and removing permeate from the permeate side of the membrane using a sweep gas or liquid. Feeds include hydrocarbon mixtures, naphtha (including virgin naphtha, naphtha from thermal or catalytic cracking, etc.).

U.S. Pat. No. 2,930,754 discloses a method for separating hydrocarbons e.g., aromatic and/or olefins from gasoline boiling range mixtures, by the selective permeation of the aromatic through certain cellulose ester non-porous membranes. The permeated hydrocarbons are continuously removed from the permeate zone using a sweep gas or liquid.

U.S. Pat. No. 4,115,465 discloses the use of polyurethane membranes to selectively separate aromatics from saturates via pervaporation.

U.S. Pat. No. 4,929,358 discloses the use of polyurethane membranes for the separation of aromatics from non-aromatics. Permeation is suggested under pervaporation, perstraction, reverse osmosis, or dialysis conditions, however none of the experimental results reported in this patent were obtained under reverse osmosis conditions.

Polyimide membranes have been used for the separation of aromatics. U.S. Pat. No. 4,571,444 discloses the separation of alkylaromatics from aromatic solvents using a polyimide polymer membrane. The polyimide membrane of choice was an asymmetric polyimide polymer membrane prepared from a fully imidized, highly aromatic polyimide copolymer. Permeation was performed under reverse osmosis conditions.

U.S. Pat. No. 4,532,029 discloses the use of an asymmetric polyimide membrane for the separation of aromatics from lower aromatic middle distillate feeds. Permeation of the feeds in the presence of a light polar solvent, e.g., acetonitrile, was required to obtain permeates having a high aromatic content, i.e., greater than 86%.

U.S. Pat. No. 4,879,044 discloses a pervaporation process for separation of heavy catalytically cracked naphtha into a highly aromatic gasoline octane blending component and a low aromatic, high cetane distillate; U.S. Pat. Nos. 4,944,880, 4,946,594, 5,039,418 and 5,093,003 disclose improvements to membrane stability at high temperatures and U.S. Pat. Nos. 5,095,171 and 5,416,259 disclose improvements to the oxidative stability of membranes.

The majority of investigations for aromatic/non-aromatic separations have involved pervaporation or perstraction separation techniques. This is probably due to reports of prior literature that very high operational pressures are required in hyperfiltration to reach an equivalent performance achievable by pervaporation and perstraction processes. Unfortunately, pervaporation and perstraction separation systems are higher cost systems than hyperfiltration systems, due to expenses associated with vacuum, refrigeration and heat transfer systems.

Consequently, it is an object of this invention to provide an improved process for the separation of aromatic hydrocarbons from non-aromatic hydrocarbons in a feed stream using asymmetric polyimide membranes.

Another object of the present invention is to provide a method of improving the feed quality to an aromatic separation or aromatic conversion process by separating non-aromatic compounds from aromatic hydrocarbons in an aromatic hydrocarbon-containing feed stream by selectively permeating at least a portion of said aromatic hydrocarbons contained in said feed stream through a permselective membrane and diverting a primarily non-aromatic retentate out of the feed stream.

Other facets and advantages of the present invention will be apparent from the ensuing description and the appended claims.

SUMMARY OF THE INVENTION

In one embodiment, the present invention is directed to a method of separating aromatic hydrocarbons from non-aromatic hydrocarbons in a feed stream by contacting a liquid feed stream containing a mixture of aromatic and non-aromatic hydrocarbons with a dense active layer of an asymmetric polyimide membrane, which membrane has been treated with a lubricating oil conditioning agent.

In another embodiment, the present invention is directed to a method of improving the feed quality to an aromatic separation or aromatic conversion process by separating non-aromatic compounds from aromatic hydrocarbons in an aromatic hydrocarbon-containing feed stream by selectively permeating at least a portion of said aromatic hydrocarbons contained in said feed stream through a permselective membrane and diverting a primarily non-aromatic retentate out of the feed stream.

In another embodiment, the present invention is directed to improving the feed quality to a hydrocarbon separation or conversion process which would benefit from a reduction in the concentration level of aromatics in the feed, by selectively permeating aromatics contained in the feed through a permselective membrane and out of the feed stream.

The present inventors have found improved asymmetric membranes which have high selectivity to permeate aromatic hydrocarbons in the presence of non-aromatic hydrocarbons. Membranes used in accordance with the invention exhibit over 30% rejection of the non-aromatic hydrocarbon materials at a commerically adequate flow rate in a temperature range of about −20 to 150° C.

Using the preferred membranes of the invention, permselective separation of aromatic hydrocarbons from non-aromatic hydrocarbons in a feed stream may be accomplished by hyperfiltration with sufficient flux and selectivity to offer improved economics over pervaporation separation conditions. However, this invention is not intended to be limited to the hyperfiltration mode of operation.

The preferred polyimide asymmetric membranes especially adapted for use in the process of the present invention are disclosed in co-pending application Ser. No. 09/126,261, entitled "Polyimide Membranes for Hyperfiltration Recovery of Aromatic Solvents", W. R. Grace-Conn. Attorney Docket No. 01-9393, filed on even date herewith, the entire contents of which are hereby incorporated by reference.

Additionally, a method is disclosed which enables lower quality feedstocks to be used in an aromatics conversion process without impacting its performance. This method involves the use of membrane-based separations to selectively remove non-aromatics introduced to the process with the feed. Compared to other processing options such as liquid/liquid extraction, membrane separation has the advantages of having significantly lower capital investment cost and energy requirements, and minimal operational impact on an existing conversion process.

BRIEF DESCRIPTION OF THE DRAWINGS

The above and other objects, features and advantages of the present invention will be better understood from the following detailed description, taken in conjunction with the accompanying drawings, all of which are given by illustration only, and are not limitative of the present invention.

FIGS. 5–7 illustrate an embodiment of the use of the present invention in an aromatics separation process, and a manner of integrating the membrane separation devices of the present invention into a hybrid aromatics separation/conversion process.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The term "aromatic" is used herein to designate a hydrocarbon-based organic compound containing one or more aromatic rings. A compound having an aromatic ring is typified by, for example, benzene. Aromatic compounds having one or more than one aromatic ring include, for example, tetrahydronaphthalene, naphthalene, anthracene, fluorene, biphenyl, pyridine, thiophene, etc. The feed to the process of the present invention is preferred to contain aromatic hydrocarbons having 1 to 2 aromatic rings.

The term "non-aromatic" is used herein to designate a hydrocarbon compound having no aromatic nucleus.

For purposes of this invention, the term "hydrocarbon" is used to mean an organic compound having a predominately hydrocarbon character. It is contemplated within the scope of this definition that a "hydrocarbon" may contain at least one non-hydrogen or non-carbon atom (e.g. sulfur or oxygen), provided that said atom(s) does not alter the predominant hydrocarbon nature of the organic compound and/or does not react to alter the chemical properties of the membrane within the context of the present invention.

A significant distinction of the present process over those of the background art is the relatively high concentration level of aromatics in the fresh feed to the membrane. As a result, a simpler hyperfiltration operation is possible and low temperatures can be used. However, in view of the relatively high aromatics concentration in the feed stream, and since the desired aromatic compounds are permeated through the membranes, it is very advantageous to utilize membranes having a high flux for aromatic compounds, in order to effectively permeate large quantities of aromatics. In contrast, the compositions which are disclosed in the background art have non-aromatics contents well above the less than 10 wt % level particularly preferred for the present process.

Processes that can take advantage of this concept include any number of aromatics conversion reactions where non-aromatics contained in the feed adversely impact performance, whether by providing a pathway for undesirable secondary reactions, by affecting catalyst aging, by reducing reaction rate due to feed dilution, by affecting product purity specifications, or by increasing the traffic in downstream recovery. The inventive concept is especially advantageous for processes that limit feed aromatics conversion to achieve a desired product selectivity or purity, and utilize recycle of the unreacted feed. In these applications, non-aromatics can build to substantial levels in the recycle stream, especially if these compounds have low reactivity in the reactor and boil within the boiling range of the recycle stream. Accordingly, it is necessary to establish a purge-off of the recycle stream to control non-aromatics buildup, which if left unchecked, would ultimately reduce unit capacity.

Examples of processes which may benefit from membrane separations according to the invention include aromatic isomerization, aromatic disproportionation, aromatic hydrogenation, aromatic alkylation and aromatic dealkylation. In these processes, it is desirable that non-aromatics content in the fresh feed is restricted to low levels.

The membranes of the invention can be used to upgrade aromatics-containing streams in petroleum refineries, such streams including naphtha streams, heavy catalytic naphtha streams, intermediate catalytic naphtha streams, light aromatic streams and reformate streams.

Benefits for selective removal of non-aromatics in the feed to an aromatics conversion process can be captured in many ways. Reducing non-aromatics buildup in the recycle loop (loop traffic) reduces the overall amount of non-aromatics to the reactor, which improves product yield and selectivity and reduces catalyst aging. Reducing loop traffic also enables additional capacity to the reactor. Alternatively, a higher non-aromatics content fresh feed can be used and selective membrane rejection brings the non-aromatics level back down to required levels. This provides increased feedstock flexibility, enabling feed from extracted and purchased sources to be backed out for less expensive, unextracted feeds. In addition, increased flexibility is given to upstream reformer operations (primary source of aromatics feed to petrochemical processes) which typically need to be run at high severities to minimize formation of non-aromatics. Accordingly, the reformer may be run under less severe conditions when the membrane separation process of the present invention is in place. Furthermore, reformate fractionation specifications can be less stringent with a more relaxed non-aromatics content target in the fresh feed.

Likewise, a benefit may be obtained in the use of the process of the present invention to enrich the non-aromatic concentration in the retentate stream. The enriched non-aromatic streams can be sent to subsequent processes which would benefit from reduced levels of aromatic compounds in the feedstream; e.g. solvent extraction units in lube processing plants.

Additionally, other refinery or petrochemical processes involving separation and/or purification of aromatic compounds, such as distillation, crystallization, extraction, adsorption or filtration processes and apparatuses, may benefit from the use of membrane separations according to the present invention. For example, placing a membrane separation device upstream of a conventional distillation column, such that the membrane separation device effects a preliminary separation of aromatics from non-aromatics, will act to unload the distillation column, increasing its effective capacity and throughput, while also improving the purity of the aromatic compounds separated by the distillation step, due to reduction or elimination of co-boiling non-aromatics from the column feed stream.

Also, hybrid processes involving aromatics, such as a hybrid aromatics conversion/separation process, a catalytic distillation process, or other hybrid adsorption, distillation, extraction or reforming processes, may benefit from the use of membranes according to the present invention. When used in a hybrid process with other separation technologies, the invention membrane is not required to make 100% separation of aromatics from non-aromatics, but can instead be used to perform partial separation of aromatics to complement overall separation processes. The membrane of the invention thus offers excellent efficiencies in bulk separation processes which when coupled with other more selective unit operations can offer enhanced performance.

Membranes suitable for the aromatics/non-aromatics separation of the process include, but are not limited to, isotropic or anisotropic materials constructed from cellulose, polyurethane, polyurea, polyimide, polyamide, polyester, polysulfone, polycarbonate, polyolefin, and copolymers thereof These can be either asymmetric or composite structures. A sample of polymeric membranes and the corresponding patent reference is given below:

| Membrane Type | U.S. Pat. No. |
| --- | --- |
| cellulose and cellulose derivatives | 2958656, 3299157 |
| polyurethane | 4115465 |
| polyurea | 312376 (EP) |
| polyurea/urethane | 4879044 |
| polyurethane-imide | 4929358 |
| polyimide | 4959151 |
| polyester-polyimide | 4990275, 5241039, 5643442 |
| polycarbonate | 5019666 |
| polsulfone | 5159130 |
| polyester-amide | 5290452 |
| fluorinated polyolefin | 5396019; | all of which are incorporated herein by reference. The membrane can also be prepared from inorganic materials including molecular sieves. A membrane with high productivity or flux is as critical to the present invention as having high permselectivity to aromatics.

An asymmetric membrane is defined for purposes of this invention as an entity composed of a dense ultra-thin top "skin" layer over a thicker porous substructure of the same or different material. Typically, the asymmetric membrane is supported on a suitable porous backing or support material.

Polyimide membranes useful in the practice of the present invention can be produced from a number of polyimide polymer sources. The identity of such polymers are presented in numerous patents. See, for example, U.S. Pat. No. 4,307,135, U.S. Pat. No. 3,708,458, U.S. Pat. No. 3,789,079, U.S. Pat. No. 3,546,175, U.S. Pat. No. 3,179,632, U.S. Pat. No. 3,179,633, U.S. Pat. No. 3,925,211, U.S. Pat. No. 4,113,628, U.S. Pat. No. 3,816,303, U.S. Pat. No. 4,240,914, U.S. Pat. No. 3,822,202, U.S. Pat. No. 3,853,754 and British Patent No. 1,434,629, all of which are incorporated herein by reference.

A preferred polyimide polymer useful to prepare the membranes of the invention is available as Matrimid 5218 from Ciba Geigy. The structure of the polyimide, Matrimid, is shown below. The polyimide is also known as the polymer with 1 (or 3)-(4-aminophenyl)-2,3-dihydro-1,3,3 (or 1,1,3)-trimethyl-1H-inden-5-amine and 5,5'-carbonylbis-1,3-isobenzofurandione repeating groups (CAS Number 62929-02-6). A common name for Matrimid is the polymer with 5(6)-amino-1-(4'-aminophenyl)-1,3,3-trimethylindane and benzophenone tetracarboxylic dianhydride repeating groups:

Matrimid 5218

Most preferably, the membranes of the invention are prepared from a polyimide polymer described in U.S. Pat. No. 3,708,458, assigned to Upjohn.

Another polyimide polymer useful in preparing preferred membranes of the present invention is available from HP Polymers, Inc., Lewisville, Tex. as Lenzing P84, which is a copolymer derived from the co-condensation of benzophenone 3,3',4,4'-tetracarboxylic acid dianhydride (BTDA) and a mixture of di(4-aminophenyl) methane and toluene diamine or the corresponding diisocyanates, 4,4'-methylenebis(phenyl isocyanate) and toluene diisocyanate. The obtained copolyimide has inide linkages and may be represented by the following repeating structural formulae:

AND

Lenzing P84 wherein the copolymer comprises from about 10 to 90% I and 90 to 10% II, preferably about 20% I and about 80% II.

Another polyimide useful to prepare a membrane in accordance with the invention is a polymer, available from HP Polymers, Inc., Lewisville, Tex. as Lenzing P84 HT. The polymer is the co-condensation product of 1H,3H-Benzo[1, 2-c:4,5-c']difuran-1,3,5,7-tetrone with 5,5'-carbonylbis[1,3-isobenzofirandione], 1,3-diisocyanato-2-methylbenzene and 2,4-diisocyanato-1-methylbenzene. The repeating groups in the structure of the polyimide are shown below.

AND

Lenzing P84 HT

The dense ultra-thin top "skin" layer of the asymmetric polyimide membranes of the invention is characterized by pore sizes below 50Å in diameter, is highly resistant to the greater than 500 psi operating pressures and has high operating efficiency and stability in the presence of solvent streams having a high aromatic content.

The preferred membranes may be conditioned by contacting with a conditioning agent dissolved in a solvent to impregnate the membrane. The conditioning agent is a lubricating oil. Lubricating oils include, for example, synthetic oils (e.g. polyolefinic oils, polyalphaolefinic oils, polyisobutylene oils, synthetic wax isomerate oils, ester oils, alkyl aromatic oils and silicone oils) and mineral oils, including solvent refined oils, hydroprocessed mineral oils and petroleum wax isomerate oils. The lubicating oil may be a light neutral oil having a boiling temperature of 400–450° C. to a heavy lubricating oil having a boiling temperature from 450–500° C. It is also within the scope of the invention to use other natural lubricating oils such as, for example, vegetable fats and oils. However, use of such fats and oils may be less desirable, due to the possibility of introducing unwanted contaminants into the process streams. Suitable solvents for dissolving the conditioning agent includes alcohols, ketones, aromatics, hydrocarbons, or mixtures thereof.

The use of a conditioning agent in accordance with the invention allows the membrane to maintain a high flux while exhibiting a high selectivity to permeate aromatics in the presence of non-aromatics. The conditioning agent also allows the membrane to be wetted with hydrocarbon solvents, to maintain a suitable pore structure in a dry state for permeation of aromatics, and to produce a flat sheet membrane with improved flexibility and handling characteristics.

Once the membranes are formed they may be processed into spiral wound modules, into hollow fiber configurations, into flat sheets or into plate and frame configurations.

The membrane process of the present invention can be operated in any of hyperfiltration, pervaporation or perstraction modes of operation.

In the practice of a preferred embodiment of the present invention, a feed stream containing the aromatic hydrocarbons and non-aromatic hydrocarbons to be separated will be contacted with the dense active layer side of the polyimide membrane under pressure and at a temperature sufficient to effect the desired separation. Such contacting will typically be at about −20° C. to about 150° C., preferably about 20° to about 80° C. The pressure employed will be at least greater than that sufficient to overcome the osmotic pressure difference between the feed stream and the permeate stream. Preferably there will be at least a net driving force of about 100 to 1000 psi across the membrane, more preferaby a net driving force of about 400 to 1000 psi most preferably about 600 to 800 psi. Preferably, no additional heating or cooling of the stream is made to minimize energy requirements.

The feed stream to be treated has at least 10 wt % aromatics and preferably contains at least 50 wt % of aromatic hydrocarbons. In a preferred embodiment, the membrane is contacted with a feed stream containing an aromatic hydrocarbon content of above 70 wt %, more preferably 80 wt %, and most preferably 90 wt % or higher. In a preferred embodiment, non-aromatics levels in the fresh feed to the membrane are below 10 wt %, and a minimum of 25% reduction, and preferably greater than 50% reduction in the non-aromatics content of the permeate is achieved.

Membranes are uniquely qualified for such separations since 2-phase formation to reject non-aromatics in a conventional aromatics extraction process may not occur at high aromatics feed concentrations (i.e., using typical extraction solvents such as sulfolane and glycol-based solvents).

Figure 1:
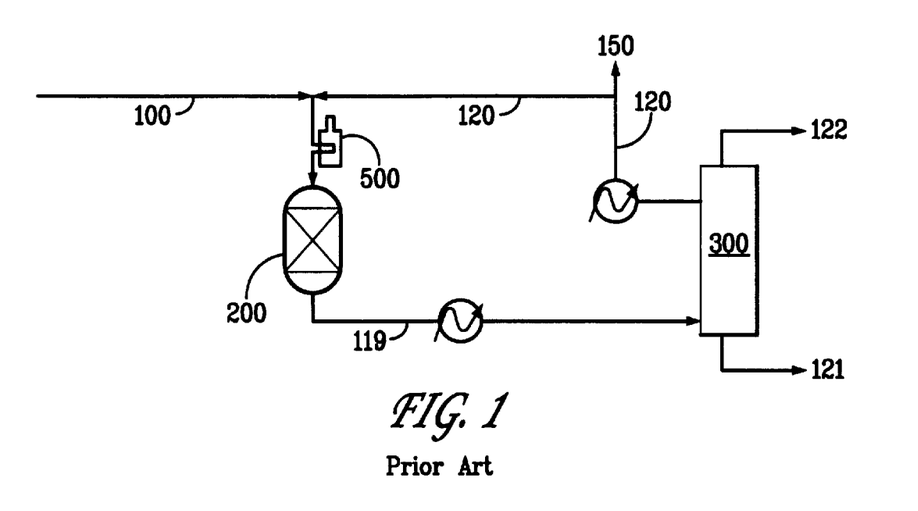
FIG. 1 (Prior Art) shows a simplified schematic of a representative process without membranes.

A number of configurations can be applied to selectively remove non-aromatics in the feed to an aromatics conversion or separation process. Some of these alternatives are depicted in FIGS. 1–4, using for illustration purposes a toluene disproportionation process feeding unextracted toluene containing non-aromatic components. FIG. 1 (Prior Art) shows a simplified schematic of the process without membranes. A distilled toluene feed stream 100 joins with a recycle stream 120, both of which are passed through a charge heater 500, to supply a toluene feedstock to disproportionation reactor 200. Products exiting reactor 200 through line 119 are piped to one or more fractionation columns 300 for separation of benzene 122 and recovery of the desired products, mixed xylenes, through line 121. An unreacted toluene recycle stream 120 is taken off of the fractionation column(s) and is provided with a non-selective purge-off 150, required to control non-aromatics buildup in reactor 200. This non-selective purge-off represents a loss in potential product yield, since some toluene will inevitably be lost.

Figure 2:
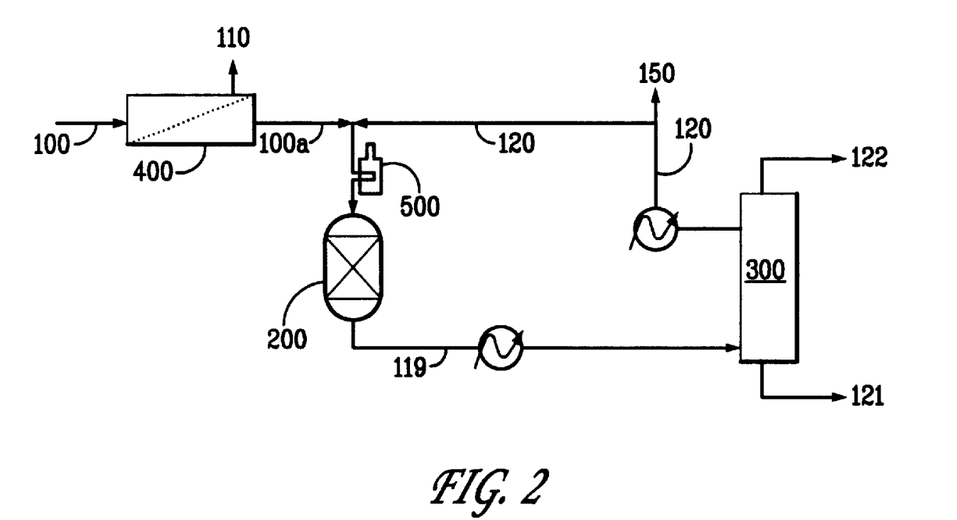
FIG. 2 shows an improved process with the membrane separations unit located upstream of the reactor to process fresh feed.

FIG. 2 shows a process modified according to the present invention with a membrane separation unit 400 located upstream of reactor 200 to process fresh feed 100. Removing non-aromatics with a purge 110 from the retentate (material not passing through membrane) side of the membrane unit 400, ahead of the reactor 200 reduces the impact of non-aromatics on the reactor and recycle purge requirements. A toluene-enriched stream 100a emerges from the permeate side of the membrane unit 400.

Figure 3:
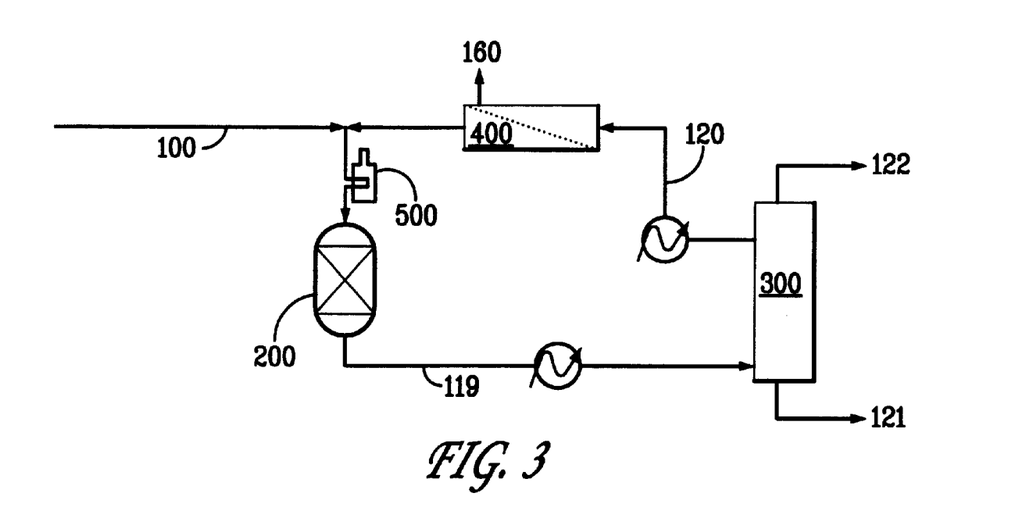
FIG. 3 shows an improved process with the membrane separation step treating an unreacted recycle stream.

FIG. 3 shows a process modified with the membrane separation unit 400 treating the unreacted toluene recycle stream 120. The non-aromatics purge-off 160 of retentate from the membrane unit will be more concentrated in non-aromatics than the purge in the Prior Art of FIG. 1. Hence, a smaller purge rate can be used to achieve a given non-aromatics removal rate. Alternatively, purge rate can be left unchanged and the higher non-aromatics removal rate enables a higher non-aromatics content feed to be used.

Figure 4:
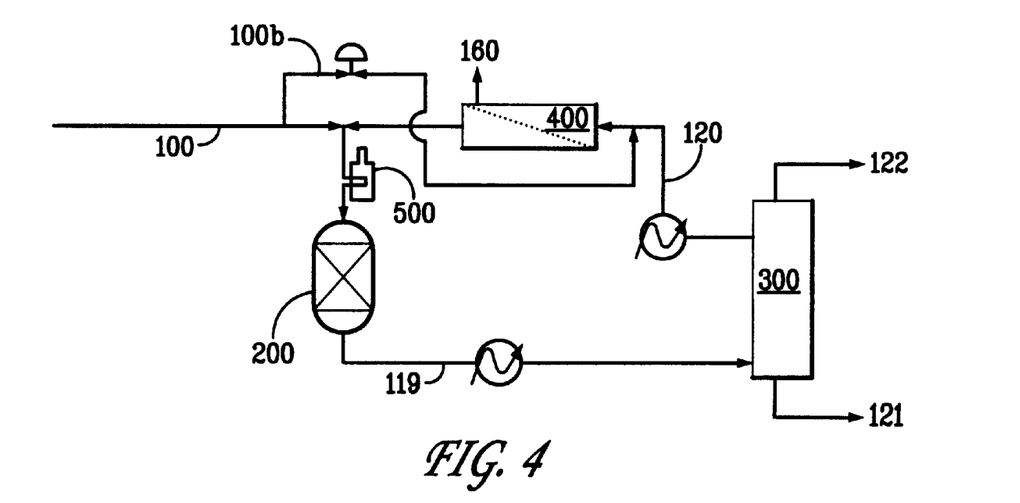
FIG. 4 shows an improved process with the membrane separation unit having the ability to process both the fresh feed and recycle feed.

FIG. 4 shows a process modified with the separation unit having the ability to process both the fresh toluene feed 100, diverted to the membrane unit 400 through auxiliary line 100b and recycle toluene feed 120 from the fractionator.

Figure 5:
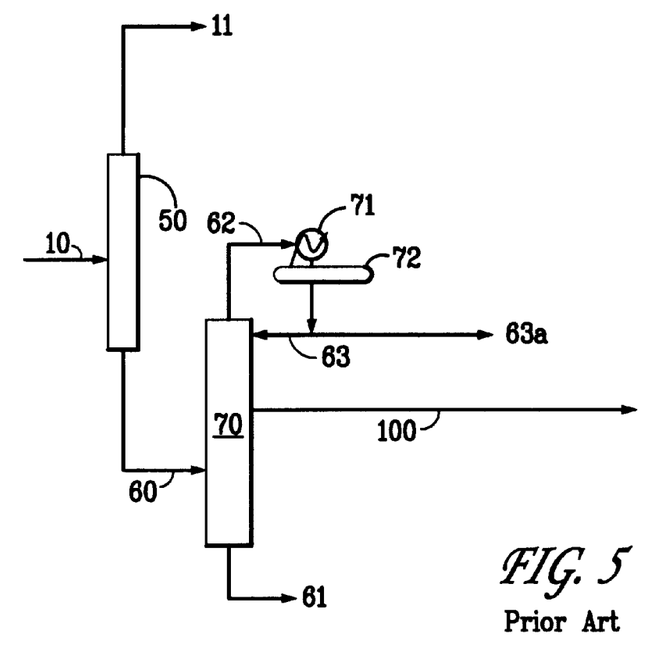
FIG. 5 (Prior Art) illustrates a conventional aromatics separation process utilizing at least one fractionation column to separate mixed boiling point hydrocarbon components.
Figure 6:
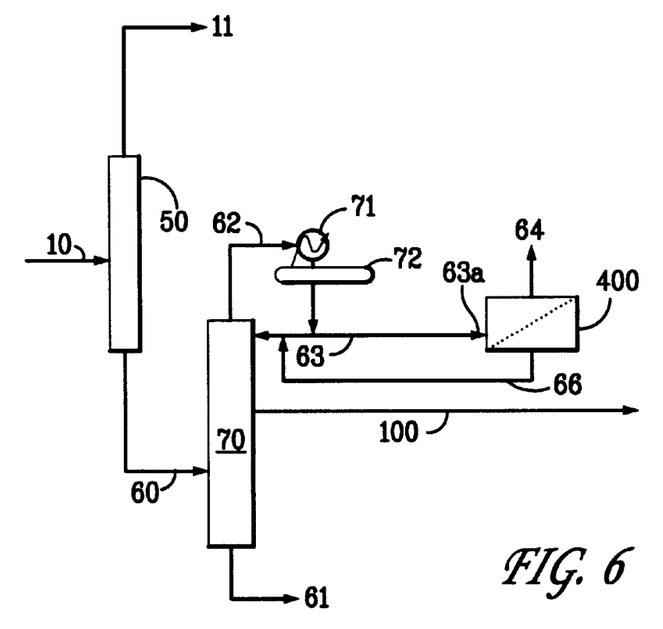
FIG. 6 shows a manner of incorporating a membrane separation unit, according to the invention, into the separation process unit of FIG. 5.
Figure 7:
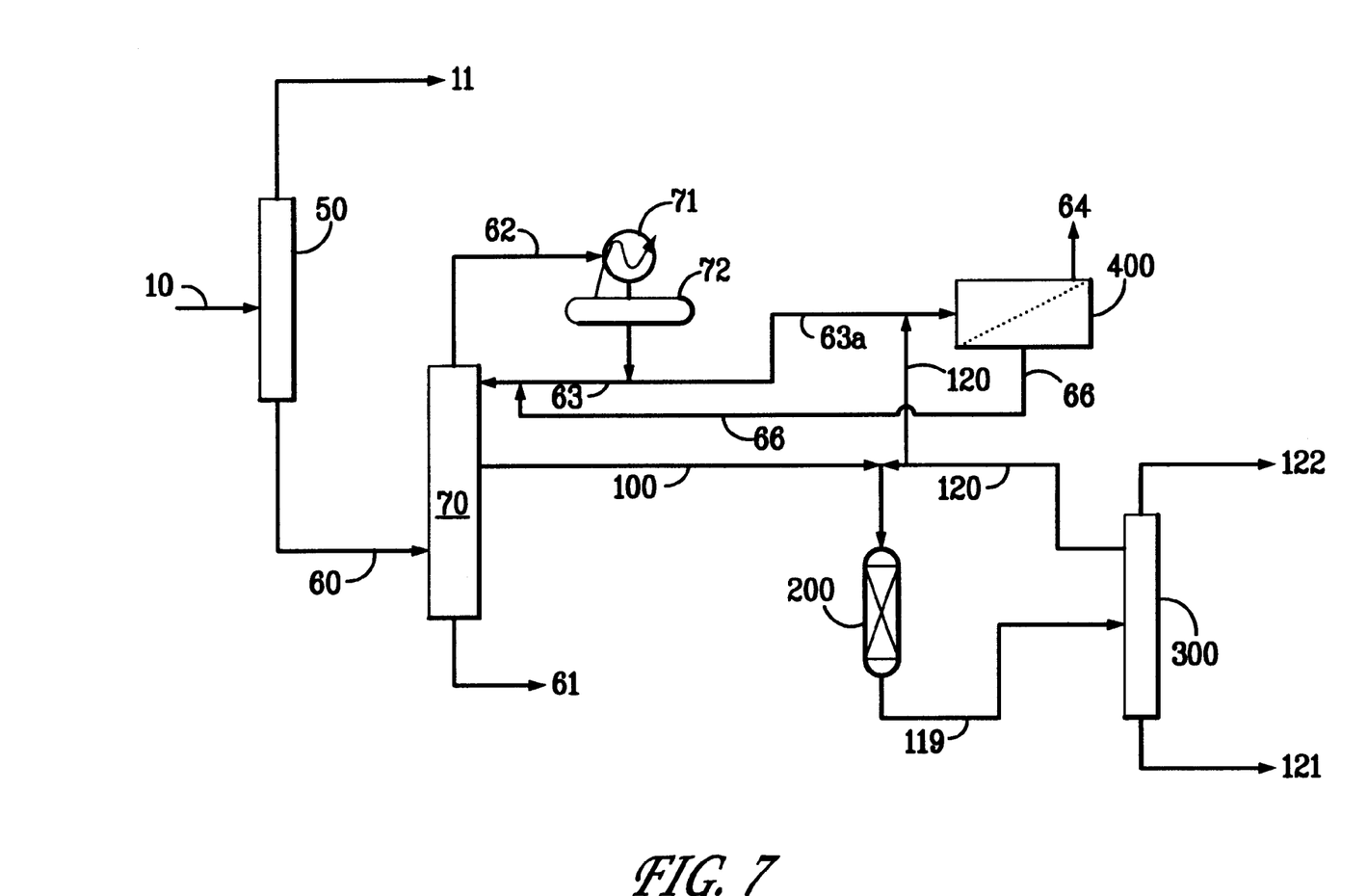
FIG. 7 shows an integrated hybrid aromatics separation/conversion unit, wherein a membrane unit according to the present invention is used in combination with both a separation unit, as illustrated in FIGS. 5 or 6, and a conversion unit, as illustrated in FIGS. 1–4.

FIGS. 5–7 illustrate an embodiment of the use of the present invention in an aromatics separation process (FIG. 6), and a manner of integrating the membrane separation devices of the present invention into a hybrid aromatics separation/conversion process (FIG. 7).

FIG. 5 is a diagram of a conventional aromatic (e.g. toluene) separation process, wherein an aromatics-containing feedstream 10, such as a product stream from a refinery reformer, is sent into a first distillation column 50. Lighter hydrocarbons such as $C_6^-$ exit the distillation column through line 11, and the remaining heavier hydrocarbons, containing the majority of the toluene, exit distillation column 50 through line 60 and are sent into a second distillation column 70. Distillation column 70 is optimized for separation of toluene, such that $C_8^+$ aromatics exit distillation column 70 through line 61, while any remaining benzene and light non-aromatics go overhead through line 62 into condenser 71 and accumulator 72 and exit through line 63a. This purge represents a loss in potential product yield since toluene will inevitably be lost. A portion of the condensed overhead vapors in line 63 may also be returned as reflux to the distillation column for further purification. Purified toluene leaves the second distillation column 70 through line 100, where it may be sent into units such as those illustrated in FIGS. 1–4.

FIG. 6 illustrates one possible enhancement to the aromatic separation unit of FIG. 5, wherein a membrane separation unit 400 is added to the process unit, such that the overhead purge from line 63a enters membrane separation unit 400, where aromatics (toluene) selectively permeate through the permselective membrane and are returned to the distillation column 70 through permeate line 66. Non-aromatics are concentrated and a purge of reduced rate is taken off in line 64.

FIG. 7 illustrates an integrated aromatics separation/conversion process unit, wherein an aromatics separation unit, such as those illustrated in FIGS. 5–6, is incorporated into an aromatics conversion unit, such as those illustrated in FIGS. 1–4. In this instance, a membrane separation unit 400 is incorporated into the system in such a manner to purify aromatics issuing from both line 63a, exiting accumulator 72 and aromatics in recycle stream 120, so as to effectively remove non-aromatics through purge-off 64 and provide purified aromatic feed back into the system through permeate line 66.

In all the options shown, a bypass around the membrane unit is incorporated (not shown) to allow control of the amount of feed that is to be processed in the membrane.

The optimum location of the membrane unit will depend on the nature of the aromatics conversion process and composition of non-aromatics in the feed. For example, for processes where non-aromatics conversions are sufficiently high such that non-aromatics levels do not accumulate appreciably in the recycle, locating the membrane on the fresh feed stream (FIG. 2) may be more advantageous. Alternately, for processes characterized by a low non-aromatics conversion level such that non-aromatics accumulate readily, locating the membrane on the recycle stream (FIG. 3) may be more beneficial. Maximum flexibility is afforded with a configuration that enables multiple streams to be directed to the membrane unit as shown in FIG. 4, either alternatively or concurrently, or by incorporating several membrane units in various locations throughout the process unit. In general, the stream with the higher non-aromatics content should be processed in the membrane to maximize non-aromatics removal.

The Examples below are for illustrative purposes only, and do not limit the invention, or the claims which follow them.

EXAMPLES

In the cases shown here, the asymmetric polyimide membranes preferentially permeate aromatic over non-aromatic hydrocarbons. The membranes were tested on a small bench unit with four (4) test cells in series under reverse osmosis conditions. The feed solution was continuously flushed over the membrane surfaces, and the permeate and retentate streams were combined and recycled. A typical feed solution consists of a high toluene concentration (80–100%), along with lesser amounts of other aromatic compounds such as benzene and p-xylene and non-aromatic hydrocarbons including branched and unbranched $C_6$ to $C_9$ isomers. The feed was pressurized, heated to operating temperatures, and pumped over the surface of the membrane. If desired, permeate lines could also be pressurized. Permeate samples were generally collected after overnight operation (18+ hours).

Membrane coupons were small disks with 14.2 $cm^2$ surface area. Flows were determined in ml/min and then converted to gallons per square foot per day (GFD). Sample sizes were kept at less than 1% by weight of material, so that retentate and feed compositions were essentially equal. GC analysis was used to identify concentrations of aromatic and non-aromatic compounds. All concentrations were expressed as weight percent and pressures indicate the differential pressure between the feed and permeate sides of the membrane, unless otherwise indicated. Rejection was calculated from the sum of non-aromatic compounds in both the permeate and retentate streams with the formula:

Rejection (%)=(1−% permeate/% retentate)×100%.

In some cases, specific rejections for a given hydrocarbon were calculated.

Example 1

A viscous solution containing 22% Lenzing P84 polyimide (HP Polymers, Inc., Lewisville, Tex.), 67% dioxane, and 11% dimethylformnamide (DMF) was prepared and filtered through a 10 micron filter. This solution was cast at 10 ft/min onto a moving web of nonwoven polyester fabric (Hollytex 3329 from Ahlstrom Filtration, Mt. Holly Springs, Pa.) using a knife blade set at a gap of 7 mil above the fabric. After about 15 seconds with an air flow of 1 SCFM the coated fabric was quenched in water at 22° C. to form the membrane structure. The membrane was washed with water to remove residual solvents, then solvent exchanged by immersion into methyl ethyl ketone (MEK) for 3 hours, followed by immersion in a solution of 20% light neutral lube oil/40% MEK/40% toluene for 3 hours. The membrane was then air dried.

The membranes were tested as flat sheet coupons at 50° C. and 800 psi with various circulating solutions consisting of a high toluene concentration and additional aromatic and non-aromatic $C_6$ to $C_9$ hydrocarbons typically found in a toluene process stream in refinery operations.

In one of the evaluations, total aromatic content in the feed was 99.37 wt %. The membrane exhibited good rejection (54%) of non-aromatics and a flux of 22.9 GFD. The aromatic content in the permeate was 99.71 wt %.

Example 2

A viscous solution containing 24% Lenzing P84 polyimide (HP Polymers, Inc., Lewisville, Tex.), 56% dioxane, and 20% dimethylformamide (DMF) was prepared. This solution was cast at 4 ft/min onto a moving web of nonwoven polyester fabric (Hollytex 3329 from Ahlstrom Filtration, Mt. Holly Springs, Pa.) using a knife blade set at a gap of 7 mil above the fabric. After about 3 seconds with an air flow of 20 SCFH the coated fabric was quenched in water at 20° C. to form the membrane structure. The membrane was washed with water to remove residual solvents, then solvent exchanged by immersion into methyl ethyl ketone (MEK) for 1 hour, followed by immersion in a 2nd solvent exchange bath of light neutral lube oil in 50/50 MEK/toluene for 1 hour. The membrane was then air dried.

A series of Lenzing P84 membranes with differing oil content were prepared by changing levels of oil in the 2nd exchange bath from 0 to 60% oil, while maintaining a 50/50 ratio of MEK/toluene.

A feed solution consisting of 88 wt % toluene with six compounds (n-decane ($C_{10}$), 1-methylnaphthalene ($C_{11}$), n-hexadecane ($C_{16}$), 1-phenylundecane ($C_{17}$), pristane ($C_{19}$), and n-docosane ($C_{22}$) each at 2 wt % levels was prepared. Coupons of each membrane were tested at 600 psi and 50° C. Results are recorded in Table 1 below.

TABLE 1

| Oil Content in 2nd Solvent Exchange Bath (%) | Flux (GFD) | $C_{10}$ Rejection (%) |
|---|---|---|
| 0 | 2.4 | 65 |
| 20 | 25.3 | 45 |
| 33 | 26.3 | 43 |
| 50 | 27.7 | 42 |
| 60 | 27.4 | 42 |

The membrane having no lube oil present as a conditioning agent had an unacceptably low flux. The membranes conditioned with lube oil exhibited over 40% rejection of non-aromatics with a significant increase in flux (GFD) over the unconditioned membrane.

Example 3

A viscous solution containing 26% Matrimid 5218 polyimide (Ciba Geigy, Hawthorne, N.Y.), 15% acetone, and 59% dimethylformamide (DMF) was prepared and filtered through a 10 micron filter. This solution was cast at 10 ft/min onto a moving web of nonwoven polyester fabric (Hollytex 3329 from Ahlstrom Filtration, Mt. Holly Springs, Pa.) using a knife blade set at a gap of 8 mil above the fabric. After about 15 seconds with an air flow of 1 SCFM the coated fabric was quenched in water at 22° C. to form the membrane structure. The membrane was washed with water to remove residual solvents, then solvent exchanged by immersion into methyl ethyl ketone (MEK) for 3 hours, followed by immersion in a solution of 20% light neutral lube oil/40% MEK/40% toluene for 3 hours. The membrane was then air dried.

A feed solution consisting of 94 wt % toluene with three non-aromatic compounds (n-decane, n-hexadecane, and n-docosane) each at 2 wt % levels was prepared. Coupons of each membrane were tested at 600 psi and 50° C.

The membrane demonstrated 25% rejection of n-decane, 51% rejection of n-hexadecane and 68% rejection of n-docosane with a flux of 18.0 GFD.

Example 4

A Lenzing P84 membrane was prepared as in Example 2 and with the 2nd solvent exchange bath containing 33% oil. An annealed membrane was prepared by clipping a sample to a glass plate, and heating in an oven at 220° C. for set times. The samples were tested with a toluene solution under pressure as in Example 2. Results are recorded in Table 2 below.

TABLE 2

Flux and Rejection for Lenzing P84 Membrane at 600 psi and 50° C.

| Anneal Time (minutes) | Flux (GFD) | Rejection (%) | | | | | |
|---|---|---|---|---|---|---|---|
| | | $C_{10}$ | $C_{11}$ | $C_{16}$ | $C_{17}$ | $C_{19}$ | $C_{22}$ |
| 0 | 29.7 | 45 | 0 | 75 | 70 | 83 | 95 |
| 2 | 19.3 | 54 | 0 | 74 | 63 | 81 | 95 |
| 4 | 17.4 | 59 | 16 | 88 | 84 | 97 | 100 |
| 6 | 9.4 | 66 | 27 | 83 | 75 | 88 | 100 |
| 8 | 3.9 | 75 | 34 | 91 | 100 | 100 | 100 |

Rejection of the non-aromatic components by the membrane increased with heat treatment of the membrane.

Example 5

An annealed Lenzing P84 membrane was prepared as in Example 4 by clipping a sample to a glass plate, and heating in an oven at 180° C. for 5 minutes. Coupons of this membrane were tested with a toluene stream obtained from a refinery. The non-aromatics in this sample were isomers of $C_7$ and $C_8$ including methyl heptanes, ethyl hexanes, dimethyl hexanes, methyl ethyl pentanes, trimethyl pentanes, methyl ethyl cyclopentanes, trimethyl cyclopentanes, and dimethyl cyclohexanes. Results are recorded in Table 3 below.

TABLE 3

Rejection and Flux for Lenzing P84 Membrane at 800 psi and 58° C.

| | Benzene (wt %) | Toluene (wt %) | p-Xylene (wt %) | wt % Non-Aromatics | Flux (GFD) | Non-Aromatics Rejection (%) |
|---|---|---|---|---|---|---|
| Feed | 0.10 | 94.89 | 0.28 | 4.73 | | |
| Permeate | 0.10 | 97.58 | 0.28 | 2.04 | 34.7 | 57 |

As shown in Table 3, the membrane exhibited favorable rejection of non-aromatics at favorable process conditions and permeate flow rates.

Example 6

A membrane as prepared in Example 1 was tested with a naphtha stream obtained from a refinery. This stream contains mostly $C_6$ to $C_{10}$ hydrocarbons which are mostly non-aromatic compounds. The major aromatic compound is toluene. Coupon tests at 800 psi and 21° C. showed the feed stream at 5.4 wt % toluene and 12.9 wt % total aromatics and the permeate stream at 6.9 wt % toluene and 16.4 wt % total aromatics with a flux of 1.3 GFD. Again, this membrane enriches aromatic over non-aromatic compounds, although it is less effective with a feed stream at low aromatics content.

Example 7

A viscous solution containing 24% Lenzing P84 HT polyimide (HP Polymers, Inc., Lewisville, Tex.), 38% dioxane, and 38% dimethylformamide (DMF) was prepared. This solution was cast at 4 ft/min onto a moving web of nonwoven polyester fabric (Hollytex 3329) using a knife blade set at a gap of 7 mil above the fabric.

After about 3 seconds with an air flow of 10 SCFH the coated fabric was quenched in water at 21° C. to form the membrane structure. The membrane was washed with water to remove residual solvents, then solvent exchanged by immersion into MEK for 1 hour, followed by immersion in a solution of 33% light neutral lube oil/33% MEK/33% toluene for 1 hour. The membrane was then air dried.

Coupons were tested with a 230–270° C. distillation cut of light cycle oil containing a high percentage of aromatic compounds. The percentage of 1-ring, 2-ring, and 3-ring aromatics and non-aromatic compounds were determined with supercritical fluid chromatography methods. Results from coupon tests at 1000 psi and 57° C. are reported in Table 4.

TABLE 4

Rejection and Flux for Lenzing P84 HT Membrane

|  | Flux (GFD) | Non-aromatics (wt %) | 1-ring aromatics (wt %) | 2-ring aromatics (wt %) | 3-ring aromatics (wt %) | Non-aromatics rejection (%) |
|---|---|---|---|---|---|---|
| Feed |  | 16.2 | 10.3 | 73.5 | 0.0 |  |
| Permeate | 1.1 | 8.5 | 8.1 | 83.4 | 0.0 | 47 |

Example 8

A viscous solution containing 22% Lenzing P84 polyimide, 11% acetone, and 67% N-methyl-2-pyrrolidone (NMP) was prepared. This solution was cast at 4 ft/min onto a moving web of non-woven polyester fabric (Hollytex 3329) using a knife blade set at a gap of 7 mil above the fabric. After about 3 seconds the coated fabric was quenched in water at 22° C. to form the membrane structure. The membrane was washed with water to remove residual solvents, then solvent exchanged by immersion into MEK for 1 hour, followed by immersion in a solution of 40% light neutral lube oil/30% MEK/30% toluene for 1 hour. The membrane was then air dried.

A feed solution consisting of 11 wt % p-xylene, 15 wt % 1-methylnaphthalene, and 74 wt % of a light neutral lube distillate obtained from a refinery was prepared. Coupons were tested at 600 psi and 107° C. The lube distillate component can be fractionated by refining processes into extract and raffinate oil. Analysis of the complex mixture as well as pure refinery extract and raffinates was done with GC and UV/visible spectrometry. By monitoring the absorption at 350 nm in methylene chloride, an estimate of the percentage of aromatic-rich extract oil and non-aromatic-rich raffinate oil in the lube distillate is determined. This is reported in Table 5.

TABLE 5

Fractionation of Lube Distillate Oil with Lenzing P84 Membrane

|  | Flux (GFD) | p-xylene (wt %) | 1-methyl naphthalene (wt %) | lube distillate (wt %) | est. wt % extract oil in lube distillate | est. wt % raffinate oil in lube distillate |
|---|---|---|---|---|---|---|
| Feed |  | 11.0 | 14.8 | 74.2 | 43.7 | 56.3 |
| Permeate | 4.1 | 12.9 | 17.4 | 69.7 | 49.8 | 50.2 |

As shown in Table 5, the membrane showed good rejection of non-aromatics as indicated by the high aromatics content in the permeate stream.

Examples 9–11

In order to confirm the efficacy and viability of using membrane separations in various locations in an aromatics-conversion process, such as depicted in FIGS. 2–4 and described above, two samples were obtained from a commercial toluene disproportionation reactor: A "fresh feed" sample, representative of a typical feed stream entering the reactor; and a "recycle feed" sample, which is representative of a portion of the product stream exiting the reactor and recycled to the input side of the reactor. Additionally, a third feed stream was synthesized by mixing the fresh feed with the recycle feed in a 50/50 weight ratio, in order to simulate the feed stream composition which would be present in FIG. 4.

Each feed was charged to a Lenzing P84 polyimide membrane coupon, prepared according to Example 1, at 60° C., under a feed pressure of 800 psig (0 psig permeate pressure) for 100 hours on stream. Results are presented in Table 6, below.

TABLE 6

Membrane Separation of Commercial Feed Streams

|  | Ex. 9 Fresh Feed | Ex. 10 Recycle Feed | Ex. 11 50/50 Fresh/Recycle |
|---|---|---|---|
| Feed Toluene (wt %) | 98.7 | 90.3 | 94.4 |
| Feed Aromatics (wt %) | 99.2 | 91.4 | 95.3 |
| Permeate Aromatics (wt %) | 99.6 | 95.5 | 98.4 |
| Non-Aromatic rejection (%) | 55.5 | 47.1 | 65.8 |
| Flux (GFD) | 25.2 | 19.1 | 19.5 |

The results also indicate an unexpected result in that processing of the fresh feed and the recycle feed together provides better membrane performance than processing either of the feeds separately. The major difference between these two feeds is that the fresh feed contains more linear and single-branched paraffins (greater than 50% of the non-aromatics are comprised of n-$C_8$ and methyl-$C_7$), while the recycle feed is more concentrated in multiple-branched paraffins and naphthenes (less than 10% of the non-aromatics are comprised of n-$C_8$ and me-$C_7$), and is predominantly multiple-branched paraffins.

Importantly, the results of the testing demonstrate that the membrane units of the present invention permit relatively high flux for aromatics, said flux being above about 10 GFD and preferably above about 15 GFD, such high flux rates being necessary for successful scale up to commercial levels. Importantly, according to the present invention, these high rates of flux are attainable with suitable aromatic selectivities to permit commercial operations.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method of separating aromatic hydrocarbons from non-aromatic hydrocarbons in a feed stream, the method comprising contacting a liquid feed stream containing a mixture of aromatic and non-aromatic hydrocarbons with a dense active layer of an asymmetric polyimide membrane, which membrane has been treated with a conditioning agent comprising a lubricating oil.

2. The method of claim 1, wherein the asymmetric membrane is prepared from a polyimide copolymer derived from the co-condensation of benzophenone 3,3', 4,4'-tetracarboxylic acid dianhydride and a mixture of di(4-aminophenyl) methane and toluene diamine or a mixture of 4,4'-methylenebis (phenyl isocyanate) and toluene diisocyanate.

3. The method of claim 2, wherein the polyimide copolymer comprises from 10 to 90% of a repeating group and from 90 to 10% of a repeating group

4. The method of claim 3, wherein the polyimide copolymer comprises about 20% of the repeating group and about 80% of the repeating group 5. The method of claim 1, wherein the lubricating oil is a synthetic oil or a mineral oil.

6. The method of claim 5, wherein the synthetic oil is a silicone oil, a polyolefinic oil, a polyalphaolefinic oil, a polyisobutylene oil, a synthetic wax isomerate oil, an ester oil or an alkyl aromatic oil.

7. The method of claim 5, wherein the mineral oil is a solvent refined mineral oil, a petroleum wax isomerate oil or a hydroprocessed mineral oil.

8. The method of claim 1, wherein the asymmetric membrane is prepared from a fully imidized polymer based on 5(6)-amino-1-(4'-aminophenyl)-1,3,3-trimethylindane and benzophenone tetracarboxylic dianhydride.

9. The method of claim 1, wherein the asymmetric membrane is prepared from a polyimide copolymer derived from the condensation of 1H,3H-Benzo difuran-1,3,5,7-tetrone with 5,5'-carbonylbis, 1,3-diisocyanato-2-methylbenzene and 2,4-diisocyanato-1-methylbenzene.

10. A method of improving the feed quality to an aromatic separation or aromatic conversion process comprising separating non-aromatic compounds from aromatic hydrocarbons in an aromatic hydrocarbon-containing feed stream by selectively permeating at least a portion of said aromatic hydrocarbons contained in said feed stream through a permselective, asymmetric Polyimide membrane under hyperfiltration conditions and diverting a primarily non-aromatic retentate out of the feed stream, wherein said membrane has been treated with a conditioning agent comprising a lubricating oil.

11. The method of claim 10, wherein said aromatics conversion reactor is any one of an aromatics isomerization reactor, an aromatics disproportionation reactor, an aromatics hydrogenation reactor, an aromatic alkylation reactor or an aromatics dealkylation reactor.

12. The method of claim 11, wherein said feed stream comprises a recycle feed stream, recycled from said aromatics conversion reactor.

13. The method of claim 11, wherein said aromatic hydrocarbon-containing feed stream comprises both a fresh feed containing aromatic hydrocarbons and a recycle feed stream from said aromatics conversion reactor.

14. The method of claim 10, wherein said aromatics separation process is at least one of distillation, crystallization, extraction, adsorption or filtration.

15. The method of claim 10, wherein said aromatic hydrocarbon-containing feed stream comprises a mixture of aromatic hydrocarbons and non-aromatic hydrocarbons having greater than 50 wt % aromatic hydrocarbons.

16. The method of claim 15, wherein said aromatic hydrocarbon-containing feed stream comprises a mixture of aromatic hydrocarbons and non-aromatic hydrocarbons having greater than 70 wt % of aromatic hydrocarbons.

17. The method of claim 10, wherein said aromatic hydrocarbon-containing feed stream is contacted with the membrane at a temperature of about −20° C., to 150° C.

18. The method of claim 17, wherein the temperature is about 20° to about 80° C.

19. The method of claim 10, wherein said aromatic hydrocarbon-containing feed stream is contacted with the membrane at a pressure sufficient to overcome the osmotic pressure difference between the permeate stream and said feed stream.

20. The method of claim 19, wherein the pressure of said aromatic hydrocarbon-containing feed stream is 100 to 1000 psi over the pressure of the permeate stream.

21. The method of claim 10, wherein said aromatic hydrocarbon-containing feed stream contains toluene.

22. The method of claim 10, wherein said aromatic hydrocarbon-containing feed stream contains two-ring aromatic compounds.

23. A method of improving feed quality to a non-aromatic hydrocarbon processing unit which would benefit from low concentration levels of aromatic hydrocarbons in said feed comprising separating aromatic hydrocarbons from non-aromatic hydrocarbons in an aromatic-containing feed stream by selectively permeating at least a portion of said aromatic hydrocarbons through a permselective, asymmetric polyimide membrane under hyperfiltration conditions and sending a retentate enriched in non-aromatic hydrocarbons to said non-aromatic processing unit.

24. The method of claim 23, wherein said retentate comprises a lube oil.

25. The method of claim 24, wherein said aromatic hydrocarbons comprise 2-ring aromatic compounds.

26. A method of improving the feed quality to an aromatic separation or conversion process comprising separating non-aromatic compounds from aromatic compounds in an aromatic hydrocarbon-containing feedstream by selectively permeating at least a portion of the aromatic hydrocarbons contained in the feedstream through a permselective membrane and diverting a primarily non-aromatic retentate off of the feedstream, wherein the membrane is an asymmetric polyimide membrane which has been treated with a conditioning agent comprising a lubricating oil.

27. An aromatics conversion process comprising the steps of:

a) passing a fresh aromatics-rich feedstream to a permselective, asymmetric polyimide membrane under hyperfiltration conditions wherein the feedstream is separated into an aromatics-enriched permeate and an aromatics-lean retentate, which membrane has been treated with a conditioning agent comprising a lubricating oil;

b) purging said retentate and passing the permeate to an aromatics conversion zone under conversion conditions;

c) passing the conversion zone product effluent stream to a product separation zone to recover converted aromatic product and a stream comprising unconverted aromatics; and d) recycling the unconverted aromatics to the aromatics conversion zone.

28. The process of claim 27 wherein the product separation zone is a distillation zone.

29. The conversion process of claim 27 wherein the unconverted aromatic stream is recycled by passing to a permselective membrane wherein the recycle stream is separated into an unconverted aromatics-enriched permeate and an aromatics-lean retentate; and passing the unconverted aromatics permeate portion of the recycle stream to the aromatics conversion zone while purging the recycle stream retentate.

30. The conversion process of claim 29 wherein a portion of the fresh feedstream is passed to the recycle stream membrane in combination with the unconverted aromatic stream recycle to separate that portion of the fresh feedstream into an aromatics-enriched permeate and an aromatics-lean retentate; and passing the combined permeate recycle stream to the conversion zone while purging the combined retentate stream.

* * * * *